United States Patent [19]

Semm et al.

[11] Patent Number: 4,676,774
[45] Date of Patent: Jun. 30, 1987

[54] APPARATUS FOR THE INSUFFLATION OF GAS

[76] Inventors: Kurt Semm, Hegewischstr. 4, D-2300 Kiel 1; Peter Neumann, Landshuterstr. 8, D-8301 Fürth, both of Fed. Rep. of Germany

[21] Appl. No.: 722,131

[22] Filed: Apr. 11, 1985

[30] Foreign Application Priority Data

Apr. 11, 1984 [DE] Fed. Rep. of Germany ....... 3413631

[51] Int. Cl.$^4$ ............................................. A61M 37/00
[52] U.S. Cl. ...................................... 604/26; 128/747; 128/748
[58] Field of Search ..................... 604/23, 26; 128/747, 128/748, DIG. 13, DIG. 12

[56] References Cited

U.S. PATENT DOCUMENTS

| | | | |
|---|---|---|---|
| 3,870,072 | 3/1975 | Lindemann | 604/26 |
| 3,885,590 | 5/1975 | Ford et al. | 604/26 |
| 3,982,533 | 9/1976 | Wiest | 604/26 |
| 4,048,992 | 9/1977 | Lindemann et al. | 604/26 |
| 4,207,887 | 6/1980 | Hiltebrandt et al. | 604/26 |

FOREIGN PATENT DOCUMENTS

| | | | |
|---|---|---|---|
| 2803646 | 8/1979 | Fed. Rep. of Germany | 604/26 |
| 1034703 | 8/1983 | U.S.S.R. | 128/748 |

OTHER PUBLICATIONS

*Basic Mechanics of Fluids,* Rouse et al, 11/1956, pp. 63-67.

Primary Examiner—C. Fred Rosenbaum
Assistant Examiner—Mario Costantino
Attorney, Agent, or Firm—Fleit, Jacobson, Cohn & Price

[57] ABSTRACT

Apparatus for the insufflation of gas, particularly carbon dioxide, into the human or animal body, by means of which the gas is passed from a pressurized gas reservoir, preferably via one or more intermediate reservoirs and at least one pressure reducer, into a line and an insufflator, e.g. a Veress needle, the intraabdominal static pressure being measured by means of the apparatus. A gas flow regulator is positioned in the line between the pressure reducer and the insufflator. Downstream of the flow regulator is positioned a pressure gauge, whose measured value is fed as a function of time into an electronic evaluation circuit and is converted into the intraabdominal pressure.

5 Claims, 1 Drawing Figure

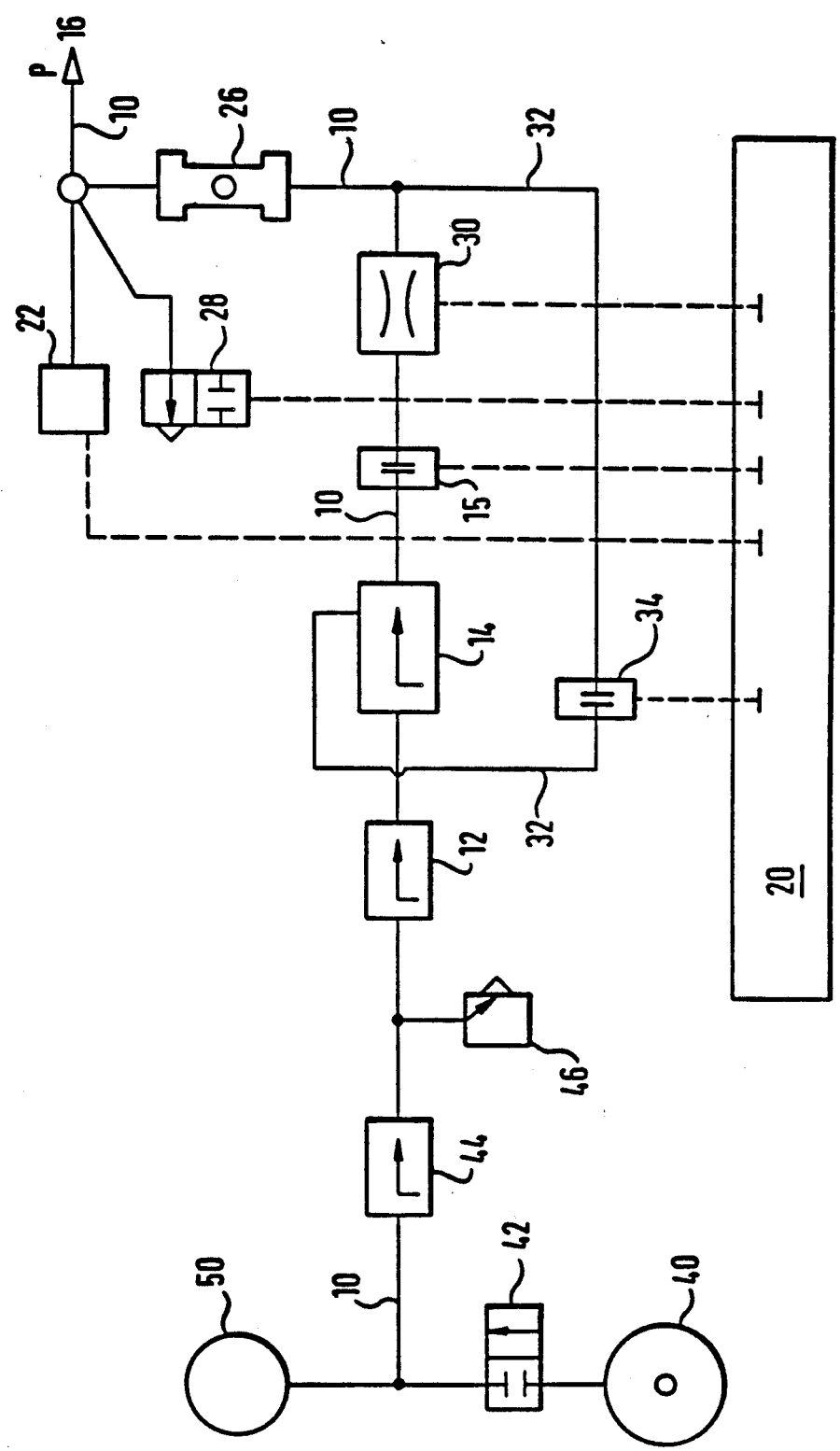

APPARATUS FOR THE INSUFFLATION OF GAS

BACKGROUND OF THE INVENTION

The invention relates to an apparatus for the insufflation of gas, particularly carbon dioxide, into the human or animal body, enabling the gas to be passed from a pressurized gas reservoir, preferably via one or more intermediate reservoirs, and at least one pressure reducer into a line and an insufflator, such as e.g. a Veress needle, the intraabdominal static pressure being measured by means of the apparatus.

Such a gas insufflation apparatus, is for example, known from German Pat. No. 28 03 646 and is used in particular to fill the abdominal cavity with gas in a controlled manner, so that endoscopic working is permitted or facilitated. It is necessary to keep the pressure constant within the abdominal cavity within physiologically acceptable limits and to accurately measure the same.

In the case of modern apparatuses of the aforementioned type, the gas is supplied to the abdominal cavity and the intraabdominal static pressure is measured by means of a single tube. According to the prior art, gas insufflation takes place intermittently and the gas flow is stopped during the intervals and the intraabdominal pressure directly measured. Although this method has proved satisfactory under various operating conditions, it still suffers from a number of disadvantages. Whilst gas is flowing into the abdominal cavity, the operator has no information on the actual pressure therein. Since during the aforementioned intermittent operation the blow-in times are much longer than the times during which the gas flow is stopped and the pressure measured, for relatively long periods the surgeon has no information on the existing static intraabdominal pressure.

SUMMARY OF THE INVENTION

The problem of the present invention is to provide an apparatus for the insufflation of gas into the human or animal body, which at all times supplies the surgeon with information on the actual static intraabdominal pressure.

According to a first variant of the invention, this problem is solved in that in the case of an apparatus for insufflation of gas of the aforementioned type, at least one gas flow rate meter is provided in the line between the pressure reducer and the insufflator (e.g. a Veress needle) and the measured gas flow rate value is fed into an electronic evaluation circuit and is converted into the intraabdominal static pressure.

The invention makes use of the finding that the flow rate in a line is dependent on the pressure gradient prevailing on either side thereof. In the case of an insufflator on one side of the line there is the pressure of an intermediate container (typically 40 mm Hg), which is optionally reduced by a pressure reducer, whilst on the other side of the line, i.e. in the vicinity of the insufflator (Veress needle), there is a lower pressure, namely the intraabdominal static pressure. The gas flow rate in the line is a clearly defined function of said pressure difference and as the higher pressure in the connection to the intermediate reservoir and the pressure reducer is determinable, intraabdominal static pressure to be measured can be gathered from this function.

Such a method for measuring the intraabdominal pressure by means of a flow rate measurement alone does, however, suffer from the disadvantages that technically flow rate measurements are relatively unreliable. It must also be borne in mind that in the case of the insufflators under discussion here, the Veress needle has a relatively small internal diameter nozzle. In addition, the flow conditions in the interior of the body in the immediate vicinity of the Veress needle are different during each insertion. Moreover, the complete line system from the pressure reducer to the insufflator can generally not be maintained constant in daily operating practice, because hoses and the like are tilted, turned over and modified. Thus, the flow resistance of the line system (which is considered to include the immediate vicinity of the Veress needle) differs between the individual operations. It is difficult to take account of these changing circumstances in the case of a flow rate measurement alone.

Thus, according to a second variant of the invention, the aforementioned problem is solved in that a flow regulator for the gas is placed in the line between the pressure reducer and the insufflator whilst downstream of the flow regulator is provided a pressure gauge, whose measured value is fed into an electronic evaluation circuit as a function of time and is converted into the intraabdominal static pressure.

Thus, according to this solution of the set problem, it is not the gas flow rate which is measured, but the static pressure in the line system upstream of the insufflator. The gas flow rate is previously regulated by means of a flow regulator to a constant, predeterminable value.

These inventive measures are based on the finding that the pressure measured in this way upstream of the insufflator is a function of the intraabdominal pressure to be measured, so that it can be correspondingly converted by means of an electronic evaluation circuit.

As a result of the aforementioned changing circumstances between the individual operations, it is generally necessary to directly measure the actual flow rate of the line system and the outlet area of the Veress needle in each individual case.

This measurement of the flow resistance of the line system in the individual case (which is mainly caused by the Veress needle) is, according to a preferred embodiment of the invention, carried out in that the measured value of the pressure meter fed into the electronic evaluation circuit is timedifferentiated and the pressure value measured at the start of insufflation at the time when the first derivative of the measured value is equal to 0, is chosen as the resistance pressure of the line and the insufflator to be associated with the apparatus.

These measures according to the invention are based on the experience that at the start of insufflation, i.e. on opening the gas supply means, initially very unstable conditions prevail, i.e. there are relatively large fluctuations in the measured value of the pressure gauge. However, shortly after, steady-state conditions occur so that the measured value of the pressure gauge is approximately constant. Thus, if the measured value of the pressure gauge is time-differentiated, then the first derivative is equal to 0 when stable flow conditions occur. However, at this time no significant intraabdominal overpressure has built up in the abdominal cavity. Thus, the pressure on the pressure gauge upstream of the insufflator is at this time solely due to the flow resistance of the line system, particularly the insufflator. Thus, the pressure value measured in this way at the start of insufflation is an apparatus constant, in which simultaneous account is taken of the flow conditions in the immediate vicinity of the insufflator. In the further course of the insufflation following the aforementioned initial conditions, the measured value of the pressure gauge gradually rises. If the pressure on the pressure gauge measured when stable flow conditions occur at the start of insufflation is designated $P_{res}$ and the rising pressure measured on the pressure gauge as insufflation advances is designated $P_{tot}$ (resistance pressure and total pressure), the static intraabdominal pressure to be measured is obtained extremely simply by subtracting the value $P_{res}$ from $P_{tot}$.

DESCRIPTION OF THE DRAWING AND PREFERRED EMBODIMENT

The invention is described in greater detail hereinafter relative to a non-limitative embodiment of the apparatus according to the invention and which is diagrammatically shown in the drawing.

A carbon dioxide gas storage bottle or cylinder 40 is opened by means of a valve 42. Carbon dioxide gas is stored in an intermediate reservoir 50. A first pressure reducer 44 reduces the high gas pressure in the intermediate reservoir 50, e.g. 0.85 bar. A safety valve 46 opens as soon as pressure reducer 44 fails. A further pressure reducer 12 reduces the pressure prevailing in line 10 to e.g. 40 or 50 mm Hg.

A flow regulator 14 is arranged in line 10 downstream of pressure reducer 12 and regulates the gas quantity flowing through per unit of time to a fixed, predeterminable value. In addition, a solenoid valve 15 is positioned in line 10 downstream of flow regulator 14, and is able to interrupt the gas flow to the patient.

A flow meter 30 measures the actual flowing gas flow and feeds the measured value into the electronic evaluation circuit 20. A flow indicator 26 positioned downstream of flow meter 30 in line 10 is used for optically checking the gas flow. Following the flow indicator 26, line 10 leads directly to the insufflator, which is not shown in detail and is symbolically indicated by reference numeral 16. The arrow P in the drawing consequently points directly to the insufflator. Furthermore, a safety valve 28 is arranged on line 10 directly upstream of the insufflator and opens on exceeding a predeterminable maximum pressure of e.g. 40 mm Hg. The pressure gauge 22 arranged upstream of insufflator 16 in line 10 is important for the invention.

Apart from main line 10, the apparatus contains a branch line 32, which connects flow regulator 14 to a point downstream of flow meter 30. An electronically operable valve 34, such as e.g. a solenoid valve, is used for blocking line 32.

Branch line valve 34, main line valve 15, flow meter 30, safety valve 28 and pressure gauge 22 are in each case connected to the electronic evaluation circuit 20. On electronic evaluation circuit 20 is provided a display, which displays the total pressure measured by pressure gauge 22, the intraabdominal static pressure determined, the gas flow rate and the total gas quantity consumed.

The apparatus shown in the drawing functions as follows. After opening the cut-off valve 42 of the $CO_2$-storage bottle 40, gas flows into intermediate reservoir 50. A first pressure reducer 44 in the line reduces the pressure to e.g. 0.85 bar. If the pressure in the line downstream of pressure reducer 44 exceeds a predetermined value, then safety valve 46 opens. A further pressure reducer 12 reduces the pressure downstream thereof, e.g., to 50 mm Hg. The following flow regulator 14 regulates the gas flow rate in line 10 to e.g. one liter/minute. The gas then flows through solenoid valve 15 and flow meter 30. The pressure drop on valve 15 and flow meter 30 as a result of the frictional resistance of the line is kept constant with the aid of the flow regulator 14 because it is always to be associated with a specific gas flow. This pressue drop is used for the flow regulation in flow regulator 14.

After the gas has flowed through the optical flow indicator 26, it passes via a hose line and the insufflator (not shown) to the patient. The hose line to the patient is indicated by arrow P.

On switching on the apparatus, i.e. on opening the bottle valve 42, the initial pressure rise is measured on pressure gauge 22 and the measured value is fed into the electronic evaluation circuit 20, where said value is differentiated as a function of time. At the start of the gas flow, there will be at least one violent fluctuation of the measured value. However, as soon as steady flow conditions have been obtained, there is only a slight change to the measured pressure value, so that the time derivative of the pressure value function measured passed towards 0. At this time, the electronic evaluation circuit 20 records the measured value on pressure gauge 22. Since at this time no significant intraabdominal static pressure has as yet built up in the abdominal cavity of the patient, the pressure value measured at the start of the stable flow conditions and stored in an analog memory in the electronic evaluation circuit is a measure of the fow resistance of the complete line system, which is mainly defined by the cross-section of the nozzle of the insufflator. The gas flow in the abdominal cavity will then produce an overpressure compared with the external atmospheric pressure which through the insufflator acts back on the pressure gauge 22. Thus on pressure gauge 22 not only is the aforementioned resistance pressure measured, but also the intraabdominal static pressure.

For determining the intraabdominal static pressure, the resistance pressure $P_{res}$ determined initially at the start of the flow is deducted from the pressure value $P_{tot}$ instantaneously measured on the pressure gauge 22. The difference directly provides the intraabdominal static pressure.

On reaching a preset pressure $P_{tot}$, the gas flow is automatically stopped by the electronic evaluation circuit, so that valve 15 closes and valve 34 in branch line 32 synchronously closes. The synchronous closing or opening of valve 15 and 34 means that the pressure value on the flow regulator 14 immediately prior to the closing of valve 15 is retained.

On reaching a certain, preselected pressure of e.g. 40 mm Hg, the instantaneous measured flow value is stored in the electronic evaluation circuit 20 and can be used for measuring the intraabdominal pressure. The intraabdominal static pressure is obtained according to the formula $$P_{abd} = P_{max} 1 - \frac{\text{instantaneous flow rate}}{\text{maximum flow rate}}$$

in which $P_{abd}$ is the intraabdominal pressure, $P_{max}$ a measured value of a maximum pressure known and limited for the instrument and the instantaneous flow rate is the actual flow rate measured at the given time, whilst the maximum flow rate is an apparatus-specific measured value for the gas flow given when $P_{max}$ is reached for the first time.

The features of the invention disclosed in the above description, claims and drawing can be essential for the realization of the invention, both individually and in random combinations.

What is claimed is:

1. An apparatus for the insufflation of gas, particularly carbon dioxide, into a human or animal body cavity, said apparatus comprising:

(a) a pressurized gas reservoir;
   (b) insufflator means communicating with said gas reservoir through a main communicating line;
   (c) pressure reducing means positioned in said main communicating line between said gas reservoir and said insufflator means for reducing the pressure of gas passing from said reservoir to said insufflation means;
   (d) gas flow rate measuring means positioned in said main communicating line between said pressure reducing means and said insufflator means for measuring the gas flow rate through said main communicating line and for providing a flow rate signal;
   (e) flow regulator means positioned in said main communicating line between said pressure reducing means and said insufflator means for regulating the rate of flow of gas to said insufflator means;
   (f) pressure measuring means positioned in said main communicating line between said flow regulator means and said insufflator means for measuring the gas pressure and providing a pressure signal representing the gas pressure at a point in said main communicating line immediately upstream of said insufflator means;
   (g) electronic evaluation circuit means connected with said pressure measuring means for receiving said pressure signal, said electronic evaluation circuit means including means for differentiating said pressure signal with respect to time to determine a line resistance reference pressure when the first time derivative of the pressure signal becomes zero immediately after the initiation of gas flow through said communicating line and before any substantial pressure increase in the body cavity, said electronic evaluation circuit means including means for receiving said flow rate signal and including display means for displaying the gas flow rate measured by said gas flow rate measuring means and for displaying intraabdominal static pressure, said electronic evaluation means further including means for determining intraabdominal static pressure by subtracting the line resistance reference pressure from the pressure measured by said pressure measuring means; and
   (h) a branch line providing communication between said main communicating line at a point downstream of said flow regulator means and said flow regulator means, said branch line including branch line shutoff valve means for controlling gas flow through said branch line.

2. An apparatus acccording to claim 1, including main communicating line shutoff valve means, and wherein the branch line shutoff valve means automatically opens and closes synchronously when the main communicating line shutoff valve means opens and closes.

3. An apparatus according to claim 2, wherein said main communicating line shutoff valve means is an electronically operable valve positioned downstream of the flow regulator means.

4. An apparatus according to claim 1 including a flow rate indicator for the flowing gas, said flow rate indicator provided in the main communicating line downstream of the flow regulator means.

5. An apparatus according to claim 1 including a safety valve provided in the main communicating line downstream of the flow regulator means.

* * * * *